United States Patent
Sparsø et al.

(10) Patent No.: US 7,115,760 B2
(45) Date of Patent: Oct. 3, 2006

(54) PROCESS FOR CONTROLLING THE FATTY ACID CHAIN COMPOSITION OF TRIGLYCERIDES AND USE THEREOF

(75) Inventors: Flemming Vang Sparsø, Skanderborg (DK); Ulrik Engelrud, Viby J (DK)

(73) Assignee: Danisco A/S, Copenhagen K (DK)

( * ) Notice: Subject to any disclaimer, the term of this patent is extended or adjusted under 35 U.S.C. 154(b) by 171 days.

(21) Appl. No.: 10/699,201

(22) Filed: Oct. 31, 2003

(65) Prior Publication Data

US 2004/0122246 A1 Jun. 24, 2004

(30) Foreign Application Priority Data

Nov. 1, 2002 (FI) ................................. 20021947

(51) Int. Cl.
*C11C 3/00* (2006.01)

(52) U.S. Cl. ..................................................... 554/169
(58) Field of Classification Search ................. 554/169
See application file for complete search history.

(56) References Cited

U.S. PATENT DOCUMENTS

| 2,879,281 A | 3/1959 | Brokaw |
| 5,968,896 A | 10/1999 | Bell et al. |
| 6,124,486 A * | 9/2000 | Cherwin et al. ............ 554/169 |
| 6,369,252 B1 | 4/2002 | Akoh |

FOREIGN PATENT DOCUMENTS

| EP | 0 466 768 B2 | 6/1999 |
| GB | 791165 | 10/1954 |
| WO | WO 01/91587 A2 | 12/2001 |
| WO | 03/029392 | 4/2003 |

OTHER PUBLICATIONS

Erciyes et al., Chimica Acta Turcica, vol. 11, pp. 191-199, 1983.*
Erciyes and Civelekoglu. "On the Molecular Distillation of Some Triglyceride Oils of Turkish Origin." Chimica Acta Turcica 1983; 11:191-199.

* cited by examiner

*Primary Examiner*—Deborah D. Carr
(74) *Attorney, Agent, or Firm*—Frommer Lawrence & Haug LLP; Thomas J. Kowalski; Angela M. Collison

(57) ABSTRACT

The present invention relates to a process for controlling the fatty acid chain composition of triglycerides wherein a feed stream comprises a mixture of triglycerides containing at least one long chain. Said mixture is substantially free of trishort chain triglycerides and it is treated in at least two fractionation steps to fractionate between long chain triglycerides at temperatures above 200° C. and pressures between 0.01 and 10 Pa, wherein one of said steps fractionates between trilong chain triglycerides and mono- and dilong chain triglycerides and the other one of said steps fractionates between monolong chain triglycerides and dilong chain triglycerides. The process can be used for the providing of target triglycerides having a controlled fatty acid chain distribution.

32 Claims, 2 Drawing Sheets

Figure 1:
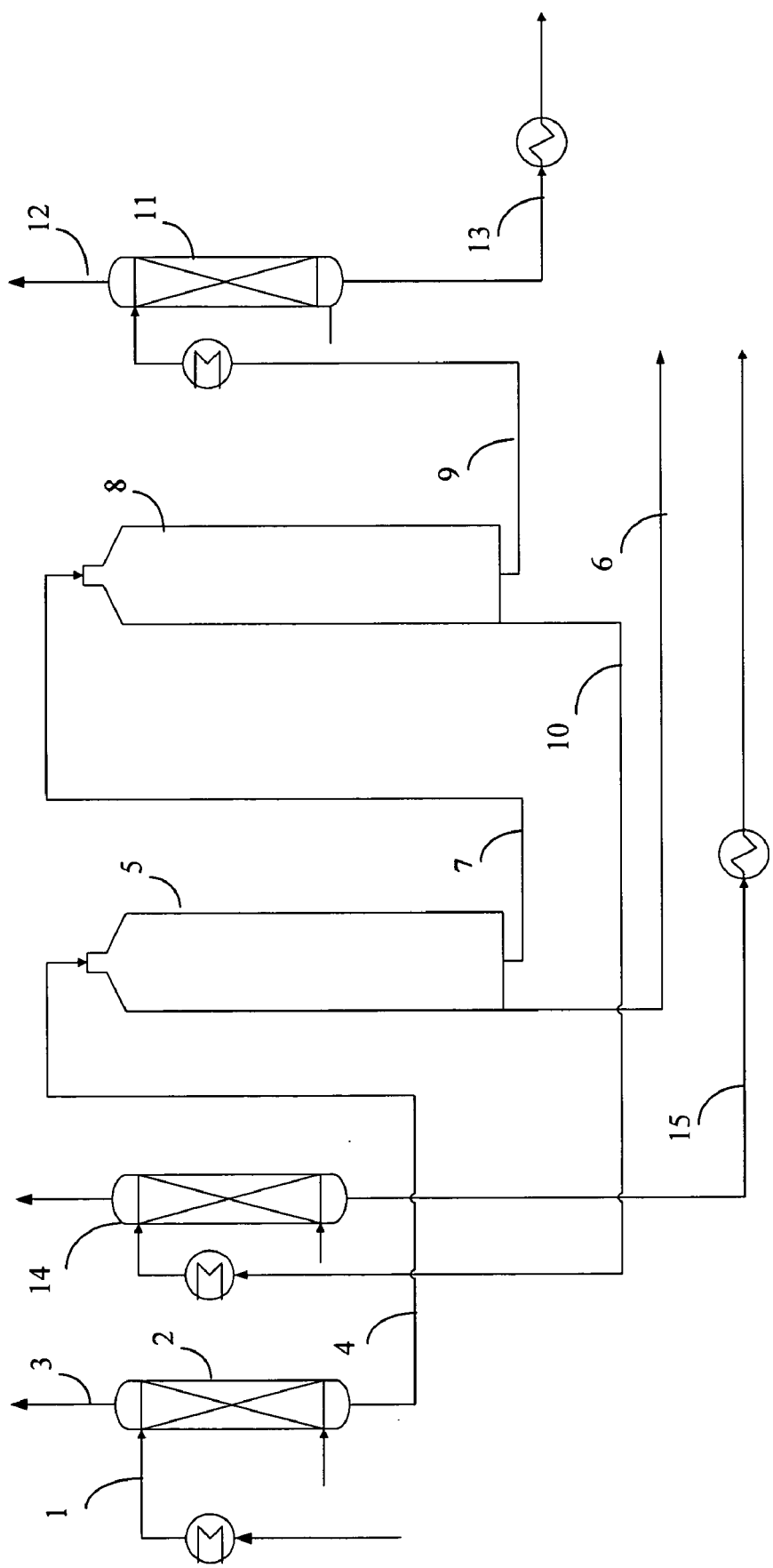

PROCESS FOR CONTROLLING THE FATTY ACID CHAIN COMPOSITION OF TRIGLYCERIDES AND USE THEREOF

REFERENCE TO RELATED APPLICATIONS

This application claims priority to Finnish Application FI20021947 filed Nov. 1, 2002.

Each of the foregoing applications, and each document cited or referenced in each of the foregoing applications, including during the prosecution of each of the foregoing applications and ("application cited documents"), and any manufacturer's instructions or catalogues for any products cited or mentioned in each of the foregoing applications and articles and in any of the application cited documents, are hereby incorporated herein by reference. Furthermore, all documents cited in this text, and all documents cited or referenced in documents cited in this text, and any manufacturer's instructions or catalogues for any products cited or mentioned in this text or in any document hereby incorporated into this text, are hereby incorporated herein by reference. Documents incorporated by reference into this text or any teachings therein may be used in the practice of this invention. Documents incorporated by reference into this text are not admitted to be prior art.

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

SUMMARY OF THE INVENTION

The invention relates to a process for controlling the fatty acid chain composition of triglycerides in order to provide a desired long chain fatty acid composition in a mixture of triglycerides. The invention also relates to the use of the process for producing of target triglycerides according to customer requirements.

BACKGROUND

The functionality and the properties of triglycerides depend on the ratio and type of fatty acid chains in the molecule. Therefore, triglycerides are used in several ways in nutrition depending on their properties. The fatty acid distribution affects e.g. the nutritional value of a triglyceride. Some fatty acids make the triglycerides high caloric whereas other fatty acids make the triglycerides low caloric. Triglycerides originating from plants etc. are typically high caloric. Triglycerides containing short and long chain fatty acids are low caloric. A special type of low caloric triglycerides are "salatrim" which include at least one long chain saturated fatty acid and at least one short chain fatty acid. Salatrim is an abbreviation of Short And Long chain Acyl TRIglyceride Molecules.

The absorbability and the digestibility of the triglycerides are affected by the fatty acid chains. Triglycerides are also sources of essential fatty acids and their metabolites like linoleic acid and α-linolenic acid, DHA (docosahexaenoic acid) and EPA (eicosapentaenoic acid). They appear in oils originating especially from sunflower, evening primrose, linseed, fish, single cell algae, etc. Thus, some triglycerides are beneficial in nutritional compositions in enteral and parenteral nutrition e.g. for surgery patients, whereas some triglycerides are used in low calorie products for controlling body weight. The fatty acid composition also affects the physical characteristics, such as the melting point of the triglycerides.

Triglycerides with specific fatty acid compositions provide advantages in the food industry, in the nutraceutical industry and the pharmaceutical industry as well as in technical applications such as coating and plasticizing etc. The use of different kinds of triglycerides for various nutritional purposes is well known in the prior art.

EP 0 466 768 relates to a synthetic triglyceride family, which can be used in parenteral nutrition or dietary supplements. The synthetic triglycerides according to the patent have at least one short chain (2–5 carbon atoms) fatty acid.

WO 01/91587 relates to a method for reducing weight gain and maintaining proper body weight, which method consists of administering to an animal an oil composition comprising triglycerides bearing short and medium chain fatty acid residues derived from fatty acids having from 4 to 14 carbon atoms and long chain fatty acid residues derived from fatty acids having from 16 to 22 carbon atoms.

U.S. Pat. No. 5,968,896 relates to a nutritional supplement containing a fat comprising at least two different fat sources of which one is an oil rich in monounsaturated fatty acids and the other is an oil rich in omega-3-fatty acids; and a therapeutic amount of antioxidant. The nutritional supplement is used for weight maintenance in individuals who are about to undergo major surgery in order to prevent or reduce postoperative complications.

Triglycerides are obtained from natural sources or they may be synthetically produced. Different processes have been developed in order to modify the fatty acid composition of triglycerides.

GB 791,165 relates to a method for the interesterification of fatty acid esters. The interesterification is performed by heating a mixture of substantially completely esterified fatty acid esters at a temperature of at least 180° C. in the presence of a plural metal soap catalyst, and thereby rearranging the fatty acid radicals in the mixture. The process according to this patent enables modification of triglycerides.

U.S. Pat. No. 6,124,486 relates to a process for making low calorie triglycerides. The process involves interesterifying short triglycerides having C2 to C10 fatty acid chains and long triglycerides having C16 to C24 fatty acid chains in the presence of a catalyst. The interesterification product mixture contains unreacted short and long triglycerides as well as individual triglycerides having at least one long and at least one short fatty acid chain. At least a substantial portion of the triglycerides has one long fatty acid chain and two short fatty acid chains. The low calorie triglycerides are then recovered from the reaction product mixture by removal of unreacted short and long triglycerides.

In the process according to U.S. Pat. No. 6,124,486 the trishort triglycerides are first removed from the reaction product mixture e.g. by evaporation. Then the remaining reaction product mixture is treated in a separation step to separate the low calorie triglycerides containing one or two long chains from unreacted trilong triglycerides and any remaining trishort triglycerides. The separation step is preferably performed in a short path still, a centrifugal molecular still or a high vacuum wiped film evaporator.

U.S. Pat. No. 6,369,252 relates to novel structured lipids and compositions comprising them as well as an enzymatic method for forming these structured lipids and mixtures. A synthetic triacylglycerol of the patent comprises at least one short chain fatty acid and at least one unsaturated fatty acid.

The prior art processes are not suitable for the preparation of pure mono- or dilong triglycerides. Only mixtures of mono- and dilong triglycerides are obtained. It is not easy to produce pure monolong triglycerides with a high yield in a one step separation process and it is impossible to produce pure dilong triglycerides in one step. It is not either possible with the prior art methods to produce pure triglycerides having a specific long fatty acid composition, which is optimal for any desired prospective use. The fractionation in the prior art is generally performed at temperatures below 270° C. Higher temperatures are generally avoided since when the separation processes are performed in the presence of an interesterification catalyst, the liquid being fractionated will at the same time undergo an interesterification reaction which continuously changes the product.

The triglyceride products obtained by the prior art chemical processes have a random fatty acid chain distribution and they include impurities such as trilong triglycerides which are not beneficial in some nutritional applications. Providing triglycerides with a certain kind of fatty acid chains as well as a specific distribution of long, medium and short chains is very difficult. Even enzymatic processes provide mixtures of triglyceride molecules.

It would be desirable to be able to produce triglycerides with various physical and chemical properties according to a predetermined pattern. However, the prior art is not exact enough for most purposes. Thus, there is a need for a method enabling the production of purer and more exactly designed triglycerides. There is especially a need for providing a process capable of producing triglycerides having a desired fatty acid chain length and composition so that any short, medium and/or long chain combination can be obtained on a commercial scale. The present invention aims at satisfying this need. There is a great interest in triglycerides in the industry and a desire to develop new triglycerides with special properties. However, the prior art processes do not enable the practitioner to obtain any target triglycerides at a level which is sufficient for practical use.

SUMMARY OF THE INVENTION

The present invention concerns a process for controlling the fatty acid chain composition of triglycerides. The process is suitable for being operated on a commercial scale. The process is defined in the appended claims. The present invention also concerns the commercial use of said process for supplying customers with their desired target triglycerides in a technically feasible way. The use is defined in the appended claims. The contents of the claims is considered as being part of this specification.

In the process according to the invention a feed stream comprising a mixture of triglycerides containing at least one long chain, said mixture being substantially free of trishort triglycerides, is treated in at least two steps for fractionating long chain triglycerides containing one, two or three long chains in consecutive fractionation means operating at temperatures above 200° C. and pressures between 0.01 and 10 Pa.

In a preferred embodiment of the invention at least one of the fractionation steps is performed at a temperature above 270° C. in order to improve the fractionation of the triglycerides containing 1 and 2 or 3 long chains, respectively. Target triglycerides having different long chain composition are recoverable from said two fractionation means, respectively, as end products.

In a preferred embodiment at least one of said fractionation steps is performed in a fractionation means, such as a distillation unit, like a short path distillation column, a centrifugal still and/or a high vacuum wiped film evaporator, preferably a short path distillation column. Fractionation steps are preferably performed in one or in two or more separate short path distillation columns. In a preferred embodiment a fluid from one of the columns is treated in another fractionation means at a temperature above 200° C. Substantially pure trilong triglyceride fractions are removed from a distillation unit operating at a temperature above 270° C.

Based on a control of the triglycerides in the feed mixture, on the temperature of the fractionation means and on the flow path of the liquids, the target triglycerides are obtained in high purity. The separation process does not affect the fatty acid composition of the triglycerides in the feed mixture. In order to obtain a desired target triglyceride, the fatty acid distribution of the feed mixture is preferably designed to provide a triglyceride mixture containing the desired monolong and/or dilong triglyceride molecules. The specific fractionation process of the invention provides the final triglyceride composition for the intended use, such as for nutritional, nutraceutical and for pharmaceutical use as well as for other uses. The process of this invention makes it possible to produce novel triglycerides in a pure form for the interested industry to test. In this way the present invention makes it possible to provide totally new triglycerides which have potentially useful and surprising properties.

In the process according to the present invention a mixture of triglycerides is fractionated in order to obtain a desired long chain fatty acid composition. The mixture of triglycerides used as a feed stream in the present invention may be prepared in any conventional manner. Thus, the mixture may be provided by interesterification of trishort and trilong triglycerides in a reaction system using conventional chemistry and/or enzymatic process, by enzymatic or chemical esterification of glycerol with short or long chain fatty acids, or by esterification of monoglycerides of long chain fatty acids with short chain fatty acids. The person skilled in the art will be aware of other ways to provide mixtures of triglycerides for the feed mixture.

Thus, the triglyceride comprising the feed stream may be provided e.g. by interesterification of trishort, trimedium and/or trilong chain triglycerides containing the desired fatty acid chains of the desired product triglyceride. The mixture obtained from a conventional esterification process contains a mixture of triglycerides comprising a different number of short, medium and long chain fatty acids depending on the feeds used for the process as well as on the process used itself.

In case the feed stream is made by interesterification, the composition of the feed stream may be optimised by selecting the ratio between trishorts and/or trimediums and trilongs in the reaction to provide the highest yield in kg/hr of the desired product in the fractionation according to the invention. When the feed stream is provided by interesterification of trishort and trilong chain triglycerides, or by other processes producing trishort chain glycerides, the present process requires the removal of the trishort compounds prior to the actual fractionation of the long chain triglycerides.

It is also possible to provide the desired feed stream mixture by enzymatic techniques. By enzymatic techniques it is, for instance, possible to obtain triglycerides containing polyunsaturated fatty acids. The enzymatic techniques also make it possible to provide a more exact distribution of the desired chains. The enzymatic techniques make it possible to produce triglyceride mixtures of long, short and/or medium chain fatty acids wherein the concentration of long chain essential fatty acids e.g. polyunsaturated fatty acids like linoleic, α-linolenic acid, DHA and EPA is higher than in a triglyceride mixture owing from chemical interesterification or esterification reactions.

In the present invention, the fatty acid composition of the final product is controlled mainly by the temperature used in the fractionation steps. The monolong, dilong and trilong chain triglycerides are separated from the mixture in an order and in fractions which depend on the temperature used in the fractionation step in question. If the trilong chain triglycerides are removed from the mixture as residue from the first fractionation step, any catalyst remaining in the mixture will be removed with the trilong compounds. Then the desired triglycerides having one or two long chain fatty acids are recovered in further fractionation steps. The number of the fractionation steps is selected according to the desired purity of the triglyceride end product.

Short chain fatty acids according to the present invention are fatty acids ranging from acetic acid (C2) to butyric acid (C4). Medium chain fatty acids are fatty acids ranging from caproic acid (C6) to decanoic acid (C10). Long chain fatty acids are acids having from 16 to 24 carbon atoms while the C12 to C14 fatty acids are intermediate and are sometimes included in the definition of long chain fatty acids.

The long chain fatty acids of the present invention are preferably C16 to C24 saturated or unsaturated fatty acids. The acids may be selected according to the desired known properties of the product which may be low caloric or other nutritional use, pharmaceutical use, etc. The acids may also be selected according to a pattern for obtaining target triglycerides with unknown properties which may prove beneficial in any field of industry.

Saturated long chain fatty acids include e.g lauric, myristic, palmitic, stearic, arachidicic, behenic, lignoceric acid, etc. Unsaturated long chain fatty acids include palmitoleic, oleic, gadoleic, arachidonic acids, etc. It is also possible to include triglycerides from oils which contain large amounts of polyunsaturated fatty acids (PUFA) such as linoleic, α-linolenic, DHA (C22:6 ω3) and EPA (C20:5 ω3), like linseed oil, sunflower oil, fish oil, algae oil, especially single cell algae oil.

In case there are no long chain fatty acids in the feed stream triglyceride mixture, then the medium chain fatty acid triglycerides can be fractionated in the same way as the long chain ones. In such a case the medium chain fatty acids should be regarded as being equivalent to long chain fatty acids as defined in the claims.

In case the triglyceride mixture contains no short chain fatty acids, the trimedium triglycerides may be removed in the same way as the trishorts.

The monolong (triglyceride) used in the specification and claims means a triglyceride having one long chain fatty acid. The two other fatty acids are either short and/or medium chain fatty acids. The dilong (triglyceride) contains two long chain fatty acids and one short or medium chain fatty acid. The trilong (triglyceride) has three long chain fatty acids. The term trishort (triglyceride) as used in the specification and claims indicates a triglyceride which contains only short chain fatty acids. The trishort and trilong triglycerides are generally not desirable in a product.

The process according to the present invention enables production of mono- and dilong triglycerides at a high purity. The process can be described in short as follows:

providing a triglyceride feed stream containing a desired mixture of triglycerides;

optionally stripping off trishort chain triglycerides from said feed stream;

subjecting the trishort-free feed stream to a first long chain triglyceride fractionation step in a first fractionation means at a temperature above 200° C.;

subjecting a fluid from said first fractionation means to a second long chain triglyceride fractionation step in a second fractionation means at a temperature above 200° C. wherein said fluid is either a distillate or a residue of said first fractionation step;

recovering target triglycerides of desired long chain composition from at least one of said first and said second fractionation means.

At least one of the fractionation steps is preferably performed at a temperature above 270° C. whereby the yield of the monolong and dilong fractions is improved and whereby the dilong concentration of the dilong fraction is increased.

The pressure in the fractionation step is lowered, preferably to a value between 0.01 and 10 Pa more preferably to a value of 0.05 to 5 Pa, most preferably to a value of 0.1 to 1 Pa.

In the distillation of the triglyceride mixture the monolongs are distilled off first. With a one step distillation of the prior art the amount of monolongs in the distillate is always high and at least 65% if the distillation is performed at a maximum temperature of 270° C. as, for instance, in the U.S. Pat. No. 6,124,486 mentioned above. Raising the temperature above 270° C. provides a higher proportion of dilongs in the product. In some cases such a mixture of mono- and dilongs is acceptable as a product. However, any residue always contains a high amount of coloured impurities.

In the present invention the fractionation is performed in two steps which improves the product purity and enables obtaining distilled products having less than 65% monolongs and more than 35% dilongs at a high yield. Although the triglyceride mixture may vary as regards the individual fatty acids contained in the triglycerides and their relative distribution in the molecule, i.e. in the 1, 2 or 3 position, the fractionation does not distinguish between the triglycerides at the distribution level. Thus, the monolongs will distill first, the dilongs thereafter and finally the trilongs. For providing a desired target monolong or dilong product, the feed triglyceride mixture is tailored accordingly to provide a suitable end product after fractionation.

The present invention enables the obtaining of a product having a purity which is higher than the purity obtainable in the prior art. The purity of the monolong and/or dilong product of the present invention is preferably at least about 75%, more preferably at least about 90%, most preferably at least about 95%.

A mixture of triglycerides obtainable from most conventional triglyceride production processes is suitable for being treated in the process according to the present invention. However, in case the mixture contains trishort triglycerides, these should be substantially removed before the mixture is subjected to the process of the invention. The mono-, di- and trilong triglycerides are each separated from the mixture in an order which depends on the flow design of the process as well as on the temperatures used in the process. The process according to the invention may be designed using conventional separation and fractionation equipment, such as distillation means and evaporators. Short path distillation units are preferred as separation means. The process preferably also includes strippers for further purification of the products.

In the preferred embodiment of the invention the two fractionation steps are performed in two separate fractionation means. It is, however, also possible to provide the two fractionation means in one and the same physical equipment. Thus it is possible to provide one short path distillation column, which has two or more separate heat sections. The separate sections may operate at different temperatures, thus providing distinct fractionation steps. The columns and/or sections may be provided with separate distillate residue collection points for recovery of the different triglycerides.

The fractionation is most preferably performed in at least two separate short path distillation columns. Depending on the desired product composition the distillation is performed at a selected temperature and with a flow design that gives the desired composition. In case short path distillation columns are used in the process according to the present invention, the fractionation is generally operated according to one of two main principles.

In one preferred process according to the invention both the mono- and the dilongs are distilled off on the first column at temperatures above about 270° C. and then the monolongs are removed from the distillate on the second column at temperatures from about 210 to 270° C. The monolongs and dilongs obtained are preferably each further purified in separate steps after the fractionation.

Another preferred way to operate the columns of the process according to the invention is to distill the majority of the monolongs on the first column. Then the dilongs are distilled from the remaining mixture on the second column. A dilong content of more than about 50%, preferably more than 75%, more preferably above about 90% is obtained with the rest being monolongs and/or trilongs. The temperature in the second column is preferably between 270 and 300° C. A higher content of dilongs is obtained if a third fractionation step is used.

The respective monolong and dilong products from the fractionation means are preferably stripped with water vapour in packed columns in order to ensure a good organoleptic quality and remove any traces of trishorts.

The present invention makes it possible to design triglycerides for any desired need and also for testing for potential beneficial properties. The process of the invention can thus be used for providing of target triglycerides having a controlled fatty acid chain distribution and composition, said use comprising the steps of
  defining at least one target long chain fatty acid of the target triglyceride(s);
  optionally defining the target position(s) of said long chain fatty acid(s);
  providing a triglyceride starting material containing a significant amount of the target triglyceride(s) having a desired fatty acid distribution;
  at need, removing trishort chain triglycerides from said starting material to provide a feed stream substantially free of trishort chain triglycerides;
  treating said feed stream in at least two fractionation steps at temperatures above 200° C. and pressures between 0.01 and 10 Pa in order to fractionate between the long chain triglycerides; and
  recovering the target triglyceride(s) containing at least one of said target long chain fatty acid(s) having the desired fatty acid distribution.

The triglycerides obtained by the present invention may be used e.g. in nutritional compositions in nutraceuticals and pharmaceuticals, etc. The triglycerides may also be used in various food industry applications, e.g. in low caloric products, in baked products, cooking oils, coatings and snack food products, as well as for emulsifiers, plasticizers etc. There are many other applications which are known to those skilled in the art. Additionally, the present invention enables the production of novel compounds having properties which are not yet known. Because the present invention provides new possibilities to obtain pure triglycerides with desired fatty acid distributions, new and hitherto unknown triglycerides with new and surprising properties may be produced. Thus, the present invention makes it possible to prepare triglycerides which are beneficial for lowering cholesterol absorption, reducing fatty tissue, reducing tumor growth rate, enhancing renal, liver or colon function or reducing the risk of infections, etc.

DETAILED DESCRIPTION OF THE INVENTION

The invention will now be described in greater detail with reference to the drawings, wherein:

FIG. 1. discloses a fractionation system for the process according to the present invention.

Figure 2:
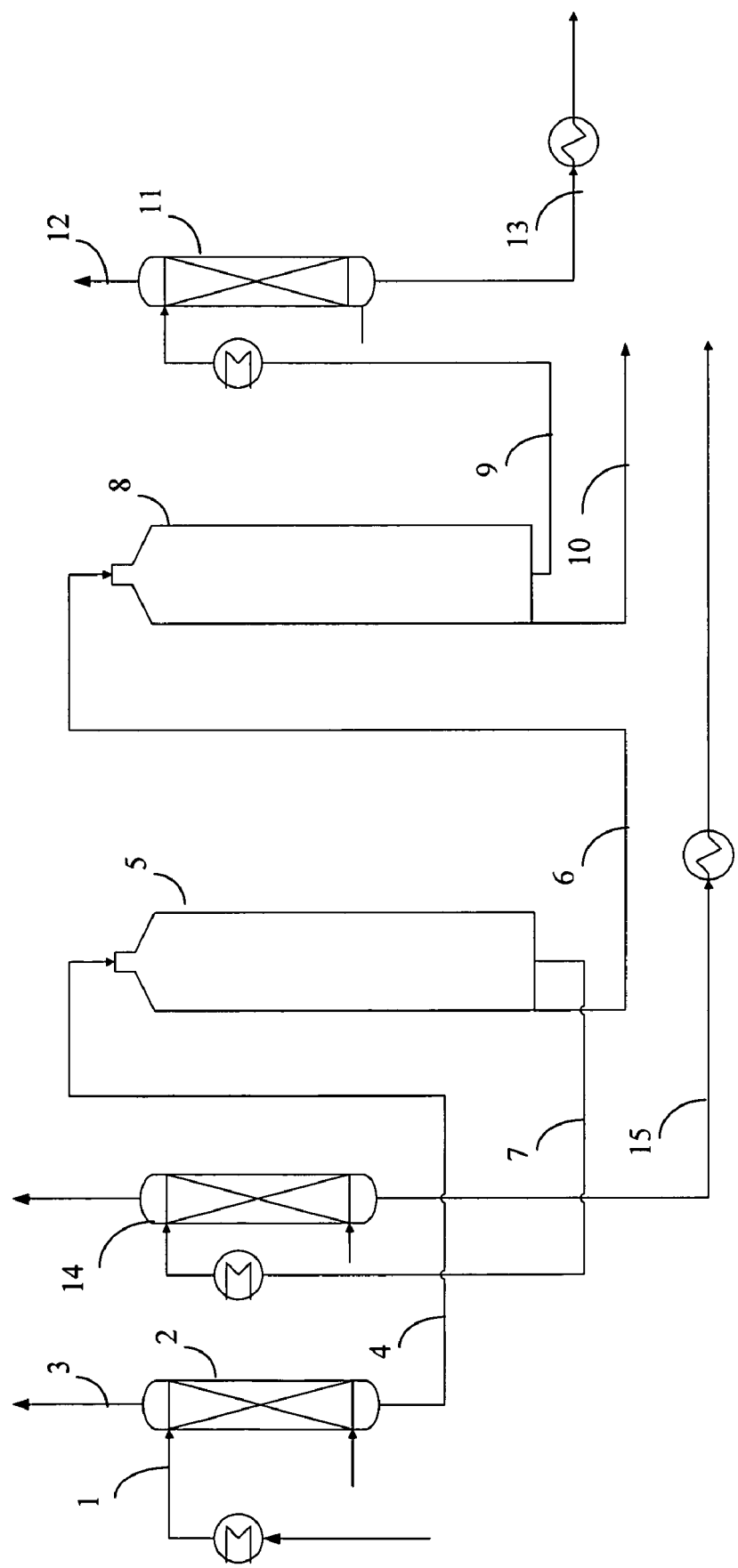

FIG. 2. discloses another fractionation system for the process according to the present invention.

In the preferred embodiment of the process disclosed in FIG. 1 a mixture 1 of triglycerides obtained from a conventional reaction system is supplied to a first stripping column 2 where substantially all of the trishorts are removed from the reaction mixture 1 at a temperature of about 180–260° C. and a pressure of about 20–1000 Pa depending on the amount of trishorts in the reaction mixture 1. In this stage about 5–40% by weight, preferably about 10–30% of the mixture is stripped off. It is preferred to remove as much as possible of the trishorts and the feed to the next step generally contains less than 0.5 weight-% trishorts. The stripped trishorts 3 may be recycled back to the process for preparing the mixture 1 of triglycerides.

The trishort-stripped mixture of triglycerides from the first stripping column 2 is used as a feed mixture 4 according to the invention. The feed mixture is first fed into a first short path distillation unit 5. The temperature of the feed is preferably adjusted to about 140–200° C. before feeding into the short path distillation. The first short path distillation is performed at a temperature of above 270° C. in order to distill both the mono- and dilongs. The pressure in the distillation unit is about 0.01–10 Pa. Trilong triglycerides are not distilled under these conditions and the residue 6 containing the trilong triglycerides is removed and may be recycled as a feed into the reaction for preparing the mixture 1 of triglycerides.

The distillate 7 containing both mono- and dilong triglycerides is then supplied to a second short path distillation unit 8. The temperature used in the second short path distillation unit is about 210–270° C. in order to distill the monolongs. The pressure in the distillation unit is about 0.01–10 Pa.

The residue 10 from the second short path distillation unit 8 is recovered as a product containing mostly dilong triglycerides. It is preferably fed to a second stripping column 14 through a heat exchanger. This stripping unit purifies the dilong triglycerides and removes the odors. The temperature of the column is about 180–240° C. and the pressure is about 20–1000 Pa. The residue 15 contains finished product comprising dilong triglycerides at a high yield.

The distillate 9 from the second short path distillation unit 8 may be supplied into a third stripping column 11 for the purification of the product. The temperature of such a column is about 180–240° C. and the pressure is about 20–1000 Pa. The residue 13 contains finished product comprising monolong triglycerides at a high yield.

In another process according to the present invention disclosed in FIG. 2, a mixture 1 of triglycerides obtained from a conventional reaction system is supplied to a first stripping column 2 where unreacted trishorts are removed from the reaction mixture 1 at a temperature of about 180–200° C. depending on the amount of trishorts in the reaction mixture.

The trishort-stripped mixture of triglycerides is used as a feed mixture 4 to a first short path distillation unit 5. The temperature of the feed is adjusted to about 140–200° C. The first short path distillation is performed at a temperature above 200° C. The pressure in the distillation unit is about 0.01–10 Pa. The monolong triglycerides are distilled off the mixture at this stage.

The distillate 7 from the first short path distillation having a temperature of about 40–100° C. may be supplied to a second stripping column 14 for purification. The temperature of the column is about 180–240° C. and the pressure is about 20–1000 Pa. The distillate is removed and the residue 15 contains finished product comprising purified monolong triglycerides.

The residue 6 from the first short path distillation unit 5 is heated to a temperature of about 140–200° C. It is then supplied to a second short path distillation unit 8. The temperature used in the second short path distillation unit is about 270–300° C. The pressure in the distillation unit is about 0.01–10 Pa. The residue contains the trilong triglycerides which may be discarded or recycled to interesterification.

The distillate 9 from the second short path distillation unit 8, having a temperature of about 40–100° C. may be supplied to a third stripping column 11 for purification. The temperature of the column is about 180–240° C. and the pressure is about 20–1000 Pa. The stripped part 12 is removed and the residue 13 contains finished product comprising dilong triglycerides.

The temperature and/or flow of the distillation is selected depending on the desired product composition. This is controlled by the distillation cut defined as the distillate flow rate in kg/hr divided by the feed flow rate in kg/hr. The mixture of triglycerides used as a feed into the fractionation process affects the amount of different long triglycerides obtained as well.

A person skilled in the art will be capable of determining the appropriate temperatures and flows for each desired product depending on the composition of the feed stream as well as the process according to the present invention.

In the following the present invention will be illustrated by some examples which describe some embodiments of the invention. The percentages in the Examples are calculated by weight unless otherwise specified.

EXAMPLE 1

A triglyceride mixture substantially free of trishort triglycerides was subjected to a two-step fractionation in accordance with the invention. The long chain fatty acids were C18 (stearic acid) and the short chain fatty acids were C4 (butyric acid). In the first fractionation the triglyceride mixture with the following composition (in weight %)
monolong 31
dilong 46
trilong 23 underwent fractionation in a short path distillation column in accordance with the principles shown in FIG. 1 at 280° C. and a pressure of 0.3 Pa. 66% of the feed was removed as distillate with a composition (%) of
monolong 49.3
dilong 48.6
trilong 2.1

The rest was a residue with the following composition (%):
monolong 0.0
dilong 39.2
trilong 60.8

The distillate from the first fractionation underwent a second fractionation in a short path distillation column at 220° C. and a pressure of 0.1 Pa. 53% of the feed was removed as distillate with a composition (%) of:
monolong 91.4
dilong 8.6
trilong 0.0

This product was recovered as a monolong triglyceride product.

The residue from the second fractionation had the following composition (%):
monolong 2.1
dilong 93.4
trilong 4.5

This product was recovered as a dilong triglyceride product. It had a dilong purity which was far higher than that obtainable by the prior art process.

EXAMPLE 2

A triglyceride mixture having the following composition (%):
trishort 11.33
free fatty acid 0.43
monolong 38.71
dilong 38.11
trilong 11.43 wherein the short chains derived from butyric acid and the long chains derived from stearic acid, was fractionated in a process according to FIG. 2. The trishorts were removed from the triglyceride mixture in a continuous stripping column at 246° C. and a pressure of 700 Pa, whereby 13% of the feed was removed as vapor containing the trishorts. The resulting liquid feed mixture had the following composition (%):
trishort 0.01
free fatty acid 0.25
monolong 41.20
dilong 44.55
trilong 13.99

The remaining liquid was separated in a first fractionation in a short path distillation column at 212° C. and a pressure of 0.1 Pa. 36.5% of the feed was removed as distillate with a composition (%) of
trishort 0.00
free fatty acid 0.30
monolong 96.50
dilong 3.20
trilong 0.00

The distillate was recovered as a substantially pure monolong product. The rest was a residue with the following composition (%):

trishort 0.00
free fatty acid 0.23
monolong 7.99
dilong 69.20
trilong 22.60

The residue was treated further in a second distillation in a short path distillation column at 218° C. and a pressure of 0.8 Pa. 10% of the residue was removed as distillate. The composition (%) of the distillate was
trishort 0.0
free fatty acid 0.8
monolong 54.4
dilong 44.8
trilong 0.0

The composition of the residue was
trishort 0.0
free fatty acid 0.2
monolong 2.8
dilong 71.9
trilong 25.1

The residue was treated in a third distillation in a short path distillation column at 259° C. and a pressure of 0.1 Pa. 43% of the residue was removed as distillate with a composition (%) of
trishort 0.00
free fatty acid 0.40
monolong 6.60
dilong 91.70
trilong 1.30

The distillate was recovered as a substantially pure dilong product.

The present invention has been illustrated in detail by the above examples. It is evident to those skilled in the art that the invention may be used in many different ways and many different applications.

Accordingly, the invention will now be further described by the following numbered paragraphs:

1. A process for controlling the fatty acid chain composition of triglycerides wherein a feed stream comprising a mixture of triglycerides containing at least one long fatty acid chain, said mixture being substantially free of trishort chain triglycerides, is treated in at least two fractionation steps to fractionate between long chain triglycerides at temperatures above 200° C. and pressures between 0.01 and 10 Pa, wherein one of said steps fractionates between trilong chain triglycerides and mono- and dilong chain triglycerides and the other one of said steps fractionates between monolong chain triglycerides and dilong chain triglycerides.

2. A process according to paragraph 1 wherein at least one of the said fractionation steps is performed at a temperature above 270° C.

3. A process according to paragraph 1 or 2 wherein at least one of said fractionation steps is performed in a fractionation means, selected from a distillation unit, a short path distillation column, a centrifugal still and a high vacuum wiped film evaporator, preferably a short path distillation column.

4. A process according to paragraph 3 wherein said fractionation steps are performed in one or in two or more separate short path distillation columns.

5. A process according to paragraph 4, wherein a fluid from one of said columns is treated in another fractionation means at a temperature above 200° C.

6. A process according to any one of the paragraphs 1 to 5 wherein the triglyceride mixture comprising the feed stream derives from an interesterification of trishort, trimedium and/or trilong chain triglycerides containing the desired fatty acid chains of the desired end product triglyceride.

7. A process according to any one of the paragraphs 1 to 6 wherein the feed stream has been stripped of trishort chain triglycerides in a stripping column to remove trishort chain triglycerides from said triglycerides before said fractionation steps.

8. A process according to paragraph 7 wherein the stripped trishort chain triglycerides comprise about 5–40%, preferably 10–30% of the triglycerides before stripping.

9. A process according to any one of the paragraphs 1 to 5 wherein the triglycerides comprising the feed stream derive from an enzymatic techniques using short and/or long fatty acid chain compounds containing the desired fatty acid chains of the desired end product triglyceride.

10. A process according to any one of paragraphs 1 to 9 wherein trishort chain stripping is performed after said fractionation steps, preferably with water vapour, preferably at a temperature of about 180–250° C. and preferably at a pressure of about 10–2000 Pa.

11. A process according to any one of paragraphs 1 to 10 wherein both monolong and dilong chain triglycerides are distilled in a first fractionation step at temperatures above 270° C. to provide a fractionation from trilong chain triglycerides.

12. A process according to paragraph 11 wherein the distillate from said first fractionation step containing both mono- and dilong chain triglycerides is supplied to a second fractionation step in order to recover the monolong chain triglycerides as distillate and the dilongs as residue at temperatures from about 210 to 270° C.

13. A process according to paragraph 12 wherein the monolong and/or dilong chain triglycerides are purified in a stripping step.

14. A process according to any one of paragraphs 1 to 10 wherein the majority of the monolong chain triglycerides are distilled off in a first fractionation step.

15. A process according to paragraph 14 wherein the monolong chain triglycerides are purified in a further step.

16. A process according to paragraph 14 or 15 wherein the residue from the first fractionation step is processed in a second fractionation step at a temperature above 270° C., preferably at a pressure of about 0.01–10 Pa, in order to recover the dilong chain triglycerides.

17. A process according to paragraph 16 wherein the dilong chain triglyceride content of the distillate after the fractionation is more than 50%, preferably more than 75%, more preferably above 90% with the rest being monolong and trilong chain triglycerides.

18. A process according to paragraph 16 or 17 wherein the distillate from the second fractionation step is supplied to a stripping step in order to purify the dilong chain triglycerides.

19. A process according to any of the preceding paragraphs wherein the feed stream to the distillation column is obtained from enzymatic or chemical processes.

20. A process according to any of the preceding paragraphs wherein a third long chain triglyceride fractionation is performed in order to obtain a purer product.

21. A process according to any of the preceding paragraphs wherein the purity of the monolong and/or dilong chain triglyceride product is at least about 75%, preferably at least about 90%, more preferably at least about 95%.

22. A process according to any of the preceding paragraphs wherein the long chain fatty acids in the triglyceride contain from 12 to 24 carbon atoms and are selected from the group consisting of lauric, myristic, palmitic, stearic, arachidic, behenic, lignoceric, palmitoleic, oleic, gadoleic, arachidonic, linoleic, α-linolenic acids and, DHA and EPA.

23. A process according to any of the preceding paragraphs wherein the short chain fatty acids in the triglyceride contain from 2 to 4 carbon atoms and are selected from the group consisting of acetic, propionic and butyric acid.

24. Use of the process according to paragraph 1 for the providing of target triglycerides having a controlled fatty acid chain distribution and composition, said use comprising the steps of
defining at least one target long chain fatty acid of the target triglyceride(s);
optionally defining the target position(s) of said long chain fatty acid(s);
providing a triglyceride starting material containing a significant amount of the target triglyceride(s) having a desired fatty acid chain distribution;
at need, removing trishort chain triglycerides from said starting material to provide a feed stream substantially free of trishort chain triglycerides;
treating said feed stream in at least two fractionation steps at temperatures above 200° C. and pressures between 0.01 and 10 Pa in order to fractionate between the long chain triglycerides; and
recovering the target triglyceride(s) containing at least one of said target long chain fatty acid(s) having the desired fatty acid chain distribution.

25. The use according to paragraph 24 wherein the target triglyceride(s) is/are recovered at a purity above 75%, preferably above 90%.

26. The use according to paragraph 24 wherein said defining of the target long chain fatty acid(s) and/or positions is done in response to customer requirements.

What is claimed is:

1. A process for controlling the fatty acid chain composition of triglycerides wherein a feed stream comprising a mixture of triglycerides containing at least one long fatty acid chain, said mixture being substantially free of trishort chain triglycerides, is treated in at least two fractionation steps to fractionate between long chain triglycerides at temperatures above 200° C. and pressures between 0.01 and 10 Pa, wherein one of said steps fractionates between trilong chain triglycerides and mono- and dilong chain triglycerides and the other one of said steps fractionates between monolong chain triglycerides and dilong chain triglycerides.

2. The process according to claim 1 wherein at least one of the said fractionation steps is performed at a temperature above 270° C.

3. The process according to claim 1 wherein at least one of said fractionation steps is performed in a fractionation means, wherein the fractionation means is selected from the groups consisting of a distillation unit, a short path distillation column, a centrifugal still and a high vacuum wiped film evaporator.

4. The process of claim 3, wherein the at least one of said fractionation steps is performed in a short path distillation column.

5. The process according to claim 3 wherein said fractionation steps are performed in one or in two or more separate short path distillation columns.

6. The process according to claim 5, wherein a fluid from one of said columns is treated in another fractionation means at a temperature above 200° C.

7. The process according to claim 1 wherein the triglyceride mixture comprising the feed stream derives from an interesterification of trishort, trimedium and/or trilong chain triglycerides containing the desired fatty acid chains of the desired end product triglyceride.

8. The process according to claim 1 wherein the feed stream has been stripped of trishort chain triglycerides in a stripping column to remove trishort chain triglycerides from said triglycerides before said fractionation steps.

9. The process according to claim 8 wherein the stripped trishort chain triglycerides comprise about 5–40% of the triglycerides before stripping.

10. The process according to claim 9, wherein the stripped trishort chain triglycerides comprises about 10–30% of the triglycerides before stripping.

11. The process according to claim 1 wherein the triglycerides comprising the feed stream derive from an enzymatic techniques using short and/or long fatty acid chain compounds containing the desired fatty acid chains of the desired end product triglyceride.

12. The process according to claim 1 wherein trishort chain stripping is performed after said fractionation steps, with water vapour, at a temperature of about 180–250° C. and at a pressure of about 10–2000 Pa.

13. The process according to claim 1 wherein both monolong and dilong chain triglycerides are distilled in a first fractionation step at temperatures above 270° C. to provide a fractionation from trilong chain triglycerides.

14. The process according to claim 13 wherein the distillate from said first fractionation step containing both mono- and dilong chain triglycerides is supplied to a second fractionation step in order to recover the monolong chain triglycerides as distillate and the dilongs as residue at temperatures from about 210 to 270° C.

15. The process according to claim 14 wherein the monolong and/or dilong chain triglycerides are purified in a stripping step.

16. The process according to claim 1 wherein the majority of the monolong chain triglycerides are distilled off in a first fractionation step.

17. The process according to claim 16 wherein the monolong chain triglycerides are purified in a further step.

18. The process according to claim 16 wherein the residue from the first fractionation step is processed in a second fractionation step at a temperature above 270° C., and at a pressure of about 0.01–10 Pa, in order to recover the dilong chain triglycerides.

19. The process according to claim 18 wherein the dilong chain triglyceride content of the distillate after the fractionation is more than 50%, with the rest being monolong and trilong chain triglycerides.

20. The process according to claim 19 wherein the dilong chain triglyceride content of the distillate after the fractionation is more than 75%, with the rest being monolong and trilong chain triglycerides.

21. The process according to claim 19 wherein the dilong chain triglyceride content of the distillate after the fractionation is more than 90% with the rest being monolong and trilong chain triglycerides.

22. The process according to claim 18 wherein the distillate from the second fractionation step is supplied to a stripping step in order to purify the dilong chain triglycerides.

23. The process according to claim 1 wherein the feed stream to the distillation column fractionation step is obtained from enzymatic or chemical processes.

24. The process according to claim 1 wherein a third long chain triglyceride fractionation is performed in order to obtain a purer product.

25. The process according to claim 1 wherein the purity of the monolong and/or dilong chain triglyceride product is at least about 75%.

26. The process according to claim 25, wherein the purity of the monolong and/or dilong chain triglyceride product is at least about 90%.

27. The process according to claim 25, wherein purity of the monolong and/or dilong chain triglyceride product is at least about 95%.

28. The process according to claim 1 wherein the long chain fatty acids in the triglyceride contain from 12 to 24 carbon atoms and are selected from the group consisting of lauric, myristic, palmitic, stearic, arachidic, behenic, lignoceric, palmitoleic, oleic, gadoleic, arachidonic, linoleic, α-linolenic acids and, DHA and EPA.

29. The process according to claim 1 wherein the short chain fatty acids in the triglyceride contain from 2 to 4 carbon atoms and are selected from the group consisting of acetic, propionic and butyric acid.

30. A method of using the process according to claim 1 for the providing of target triglycerides having a controlled fatty acid chain distribution and composition, said use comprising the steps of defining at least one target long chain fatty acid of the target triglyceride(s);

optionally defining the target position(s) of said long chain fatty acid(s);

providing a triglyceride starting material containing a significant amount of the target triglyceride(s) having a desired fatty acid chain distribution;

at need, removing trishort chain triglycerides from said starting material to provide a feed stream substantially free of trishort chain triglycerides;

treating said feed stream in at least two fractionation steps at temperatures above 200° C. and pressures between 0.01 and 10 Pa in order to fractionate between the long chain triglycerides; and recovering the target triglyceride(s) containing at least one of said target long chain fatty acid(s) having the desired fatty acid chain distribution.

31. The method according to claim 30 wherein the target triglyceride(s) is/are recovered at a purity above 75%.

32. The method according to claim 30 wherein the target triglyceride(s) is/are recovered at a purity above 90%.

* * * * *